United States Patent
Lee et al.

(10) Patent No.: US 10,393,689 B2
(45) Date of Patent: Aug. 27, 2019

(54) SEMICONDUCTOR GAS SENSOR AND METHOD OF MANUFACTURING THE SAME

(71) Applicant: DONGBU HITEK CO., LTD., Seoul (KR)

(72) Inventors: Joo Hyeon Lee, Gyeonggi-do (KR); Han Choon Lee, Seoul (KR)

(73) Assignee: DB HITEK CO., LTD., Seoul (KR)

( * ) Notice: Subject to any disclaimer, the term of this patent is extended or adjusted under 35 U.S.C. 154(b) by 0 days.

(21) Appl. No.: 15/414,104

(22) Filed: Jan. 24, 2017

(65) Prior Publication Data
US 2017/0212070 A1    Jul. 27, 2017

(30) Foreign Application Priority Data
Jan. 27, 2016 (KR) .................. 10-2016-0010255

(51) Int. Cl.
*G01N 27/12* (2006.01)
*H01L 29/66* (2006.01)

(52) U.S. Cl.
CPC ......... *G01N 27/125* (2013.01); *G01N 27/128* (2013.01); *H01L 29/66007* (2013.01); *G01N 27/123* (2013.01)

(58) Field of Classification Search
CPC ............ H01L 29/66007; G01N 27/125; G01N 27/128; G01N 27/123
See application file for complete search history.

(56) References Cited

U.S. PATENT DOCUMENTS

| | | | | |
|---|---|---|---|---|
| 4,580,439 A | * | 4/1986 | Manaka | G01N 27/12 338/34 |
| 7,963,147 B2 | * | 6/2011 | Jun | G01N 27/128 73/25.01 |
| 2008/0233752 A1 | * | 9/2008 | Ko | B81C 1/00801 438/700 |
| 2017/0234821 A1 | | 8/2017 | Lee et al. | |

FOREIGN PATENT DOCUMENTS

KR      100812996 B1     3/2008
KR    1020090061865 A    6/2009

OTHER PUBLICATIONS

Application and File History for U.S. Appl. No. 15/414,125 filed Jan. 24, 2017. Inventors: Lee et al.

* cited by examiner

*Primary Examiner* — Marcos D. Pizarro
*Assistant Examiner* — Antonio B Crite
(74) *Attorney, Agent, or Firm* — Patterson Thuente Pedersen, P.A.

(57) ABSTRACT

In embodiments, a semiconductor gas sensor includes a substrate having a cavity, a first insulation layer formed on the substrate, including an exposure hole formed at a position corresponding to the cavity and a peripheral portion of the cavity, a second insulation layer formed on the first insulation layer, covering the exposure hole, a heating electrode formed on the second insulation layer, being formed at a position corresponding to the cavity, a sensing electrode formed over the heating electrode, being electrically insulated from the heating electrode and a detection layer covering the sensing electrode, being capable of having a variable resistance when acting with a predetermined kind of gas.

19 Claims, 6 Drawing Sheets

SEMICONDUCTOR GAS SENSOR AND METHOD OF MANUFACTURING THE SAME

CROSS-REFERENCE TO RELATED APPLICATION

This application claims priority to Korean Patent Application No. 10-2016-0010255, filed on Jan. 27, 2016, and all the benefits accruing therefrom under 35 U.S.C. § 119, the contents of which are incorporated by reference in their entirety.

TECHNICAL FIELD

The present disclosure relates to a semiconductor gas sensor and a method of manufacturing the gas sensor, and more particularly, to a semiconductor gas sensor capable of detecting a gas using a oxide semiconductor material to be used for detecting a particular kind of gas and a method of manufacturing a semiconductor gas sensor.

BACKGROUND

Generally, a semiconductor gas sensor can detect a gas using an oxide semiconductor material having a variable resistance when contacting a particular kind of gas. The semiconductor gas sensor can be manufactured through a semiconductor manufacturing process. The semiconductor gas sensor has advantages of having relatively small size, low manufacturing costs, a high sensitivity and a high response speed.

The semiconductor gas sensor includes a substrate, a heating electrode, a sensing electrode formed over the heating electrode, a detection layer to cover the sensing electrode, and a plurality of insulation layers stacked on the substrate. The detection layer is a member to substantially detect gas and is formed using an oxide semiconductor material. While the detection layer is exposed to gas, gas can be adsorbed to a surface of the detection layer to have a value of the resistance varied to detect whether gas exists. In particular, the semiconductor gas sensor may be required to maintain a temperature of the detection layer over 300° C. in order to secure a gas detection, thus that it may be necessary for the heating electrode formed under the detection layer to generate heat to be transmitted to the detection layer for an efficient detection of the detection layer.

However, the semiconductor gas sensor may be damaged because the durability of the semiconductor gas sensor may be deteriorated due to heat. In order to improve the thermal durability of the semiconductor gas sensor, the semiconductor gas sensor may have a cavity formed under the heating electrode to dissipate heat from the heating electrode. The cavity may be formed by partially removing the substrate and a plurality of insulation layers stacked on the cavity may cover the cavity to form a membrane structure.

A portion covering the cavity may not be stably supported by the substrate such that a membrane structure formed over the cavity may sag. Thus, a sag phenomenon occurred to the membrane may be caused by a thermal stress or an intrinsic stress which the membrane has.

In particular, the heating electrode may be required to keep a resistance uniform in order to transmit heat to the sensing electrode stably. When the membrane sags, the resistance of the heating electrode disposed in the membrane may vary, and thus it may be difficult for the heating electrode to provide heat for the sensing electrode stably. Further, due to the sag of the membrane, a heated area of the sensing electrode may deform such that a temperature distribution of the sensing area is non-uniform.

SUMMARY

The present disclosure provides a semiconductor gas sensor capable of keeping a temperature of a sensing area constant and a temperature distribution of a sensing area uniform and a method of manufacturing a semiconductor gas sensor.

In accordance with an aspect of the present invention, a semiconductor gas sensor includes a substrate having a cavity, a first insulation layer formed on the substrate, including an exposure hole formed at a position corresponding to the cavity and a peripheral portion of the cavity, a second insulation layer formed on the first insulation layer, covering the exposure hole, a heating electrode formed on the second insulation layer, being formed at a position corresponding to the cavity, a sensing electrode formed over the heating electrode, the sensing electrode being electrically insulated from the heating electrode and a detection layer covering the sensing electrode, and the sensing electrode further being capable of having a variable resistance when interacting with a predetermined kind of gas.

In an example embodiment, the semiconductor gas sensor may further include at least one protrusion portion protruded from a face of the second insulation layer, the protrusion portion being formed at a position corresponding to the peripheral portion of the cavity to suppress the second insulation layer from sagging down to the cavity.

In an example embodiment, the protrusion portion may be formed in the exposure hole to face the substrate.

In an example embodiment, the protrusion portion may be spaced apart from a face of the substrate.

In an example embodiment, the protrusion portion may make contact with a face of the substrate.

In an example embodiment, a plurality of protrusion portions may be formed along a circumferential line of the cavity and being apart from one another.

In an example embodiment, the protrusion portion may be apart from the first insulation layer.

In an example embodiment, the protrusion portion may have a column shape.

In an example embodiment, the protrusion portion may be integrally formed with the second insulation layer.

In an example embodiment, each of the cavity and the exposure hole may have a cylindrical shape.

In an example embodiments, the semiconductor gas sensor may further include a heating pad formed on the second insulation layer and out of the exposure hole, the heating pad being electrically connected to the heating electrode, a sensing pad formed being coplanar with the sensing electrode, the sensing pad being electrically connected with the sensing electrode, and a third insulation layer being formed on the second insulation layer having the heating electrode and the heating pad, and including a face on which the sensing electrode and the sensing pad is formed, such that the third insulation layer insulates the heating electrode from the sensing electrode.

In an example embodiment, one of the first and the second insulation layers may include silicon oxide and the other of the first and the second insulation layers may include silicon nitride.

In accordance with an aspect of the present invention, a semiconductor gas sensor is manufactured by forming a first insulation layer on a face of a substrate, forming a second insulation layer on the first insulation layer, forming a heating electrode on the second insulation layer, the heating electrode being capable of generating heat, forming a sensing electrode over the heating electrode, being insulated from the heating electrode, patterning the substrate to form a cavity under the heating electrode, removing a portion of the first insulation layer which is exposed by the cavity and corresponds to a peripheral portion of the cavity to form an exposure hole and forming a detecting electrode covering the sensing electrode, the detecting electrode having a variable resistance when interacting with a predetermined kind of gas.

In an example embodiment, prior to forming the second insulation layer, the first insulation layer may be patterned to form at least one mold hole for forming a protrusion portion at a face of the second insulation layer, wherein the mold hole is formed at a position corresponding to the peripheral portion of the cavity and at a portion of the first insulation layer, and forming the exposure hole may include forming the protrusion portion in the exposure hole by removing a portion of the first insulation layer adjacent to the protrusion portion.

In an example embodiment, the mold hole may have a recess shape such that the protrusion portion is apart from a face of the substrate.

In an example embodiment, the mold hole may have a penetration-hole shape to partially expose the substrate such that the protrusion portion makes contact with a face of the substrate.

In an example embodiment, a plurality of mold holes may surround a portion of the first insulation layer corresponding to the cavity and may be apart from each other.

In an example embodiment, forming the heating electrode may include forming a heating pad on the second insulation layer and outside from the exposure hole and the heating pad being electrically connected with the heating electrode, and forming the sensing electrode may include forming a sensing pad being electrically connected with the sensing electrode.

In an example embodiment, forming the exposure hole may include patterning the first insulation layer through a wet etch process using the substrate having the cavity as an etch mask.

In an example embodiment, the first insulation layer may be formed using a material different from that of the second insulation layer.

According to example embodiments, the semiconductor gas sensor includes an exposure hole to relieve sag of a membrane toward a cavity. Further, the semiconductor gas may include a plurality of protrusion portions to support a second insulation layer formed beneath a lower face of the second insulation layer to alleviate sag of the membrane.

Therefore, a heating electrode can maintain a resistance uniformly to provide heat with a detection layer to keep the temperature constant. Thus, the temperature distribution of an area of the sensing electrode to be provided with heat will not vary because the detection layer generates heat uniformly. As a result, the semiconductor gas sensor has a thermal durability and does not suffer from thermal damage.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Hereinafter, specific embodiments will be described in more detail with reference to the accompanying drawings. The present invention may, however, be embodied in different forms and should not be construed as limited to the embodiments set forth herein.

As an explicit definition used in this application, when a layer, a film, a region or a plate is referred to as being 'on' another one, it can be directly on the other one, or one or more intervening layers, films, regions or plates may also be present. Unlike this, it will also be understood that when a layer, a film, a region or a plate is referred to as being 'directly on' another one, it is directly on the other one, and one or more intervening layers, films, regions or plates do not exist. Also, though terms like a first, a second, and a third are used to describe various components, compositions, regions and layers in various embodiments of the present invention are not limited to these terms.

Furthermore, and solely for convenience of description, elements may be referred to as "above" or "below" one another. It will be understood that such description refers to the orientation shown in the Figure being described, and that in various uses and alternative embodiments these elements could be rotated or transposed in alternative arrangements and configurations.

Similarly, the terms "upper" and "lower" are used in some embodiments. These terms are used to refer to the orientation as shown in the figures, and not necessarily any upper or lower orientation in any other reference frame. It will be understood by one of ordinary skill in the art that embodiments could be used in any orientation with respect to a gravitational or other reference frame without deviating from the scope of the invention described herein.

In the following description, the technical terms are used only for explaining specific embodiments while not limiting the scope of the present invention. Unless otherwise defined herein, all the terms used herein, which include technical or scientific terms, may have the same meaning that is generally understood by those skilled in the art.

The depicted embodiments are described with reference to schematic diagrams of some embodiments of the present invention. Accordingly, changes in the shapes of the diagrams, for example, changes in manufacturing techniques and/or allowable errors, are sufficiently expected. Accordingly, embodiments of the present invention are not described as being limited to specific shapes of areas described with diagrams and include deviations in the shapes and also the areas described with drawings are entirely schematic and their shapes do not represent accurate shapes and also do not limit the scope of the present invention.

Figure 1:
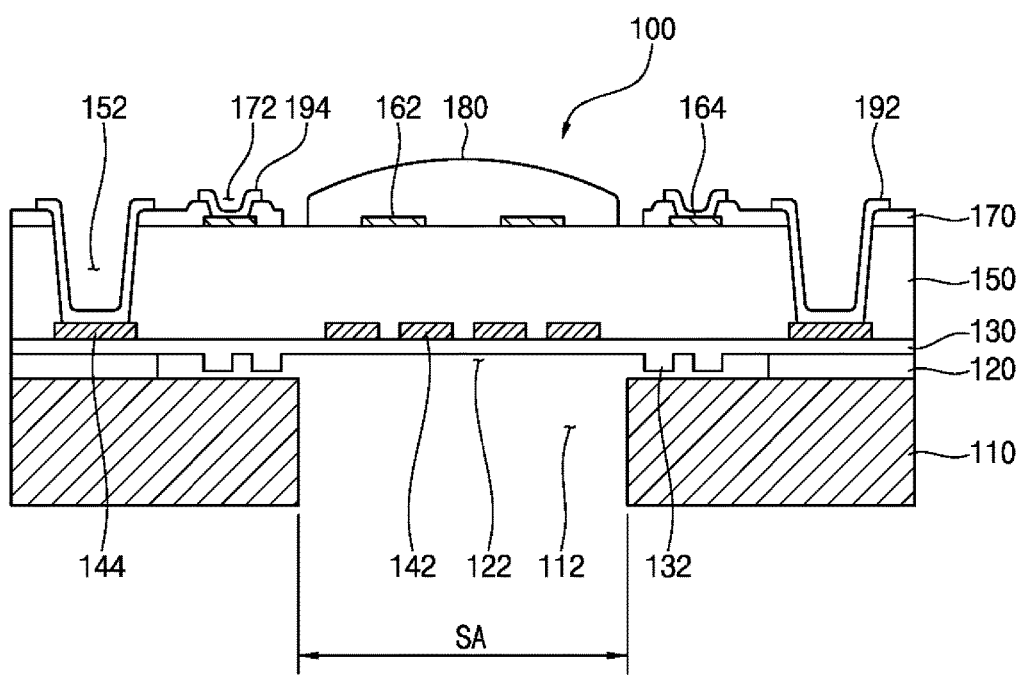
FIG. 1 is a cross-sectional view illustrating a semiconductor gas sensor in accordance with an example embodiment of the present invention.
Figure 2:
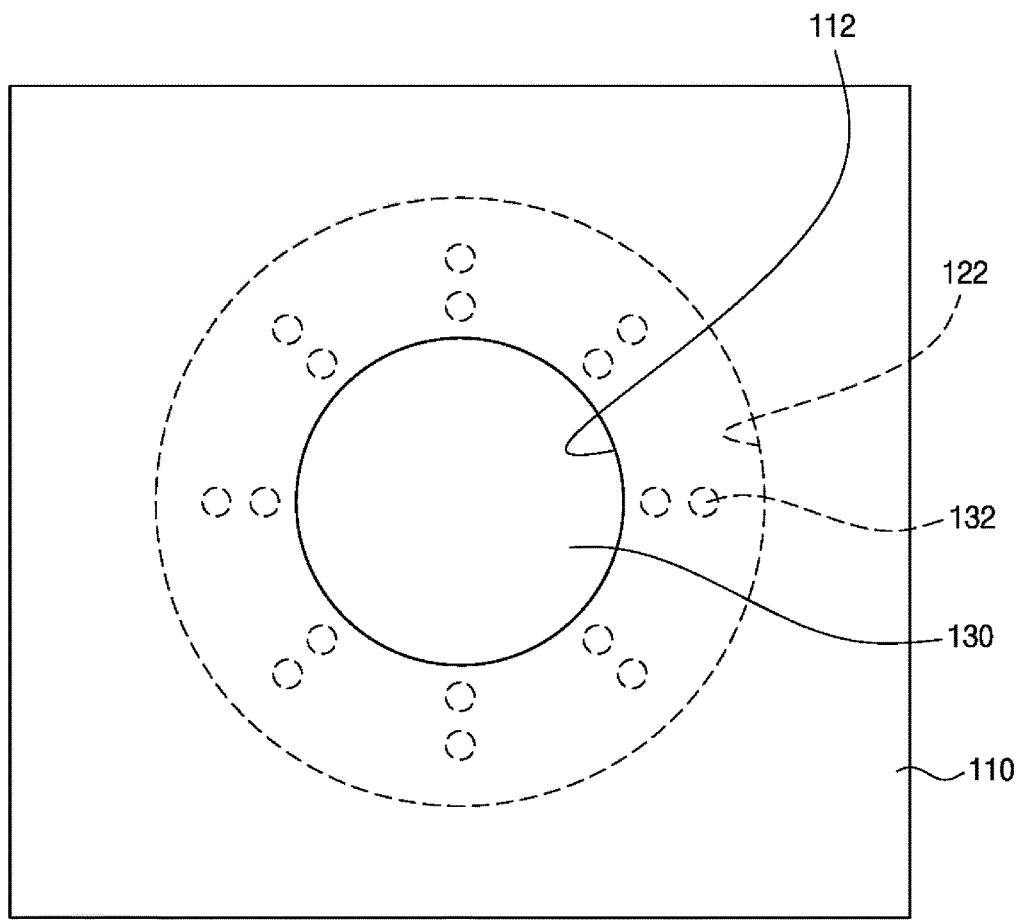
FIG. 2 is a bottom view illustrating the semiconductor gas sensor as shown in FIG. 1.

FIG. 1 is a cross-sectional view illustrating a semiconductor gas sensor in accordance with an example embodiment of the present invention. FIG. 2 is a plan view illustrating a positional relation among a cavity, an exposure hole and protrusion portions in FIG. 1.

Referring to FIGS. 1 and 2, a semiconductor gas sensor 100 in accordance with an example embodiment of the present invention is capable of detecting a gas using an oxide semiconductor material. The semiconductor gas sensor 100 can be manufactured through a semiconductor manufacturing process.

The semiconductor gas sensor 100 includes a substrate 110, a first insulation layer 120, a second insulation layer 130, one or more heating electrodes 142, a sensing electrode 162, and a detection layer 180.

In particular, the substrate 110 may include silicon material and include a cavity 112 which may be formed by a patterning process of removing a portion of substrate 110.

The first insulation layer 120 and the second insulation layer 130 are sequentially formed on the substrate 110. The first insulation layer 120 includes an exposure hole 122. The exposure hole 122 may be formed by removing a portion of the first insulation layer 120, corresponding to the cavity 122 and a peripheral portion of surrounding the cavity 112. The exposure hole 122 may fluidically communicate with the cavity 112. The cavity 112 and the exposure hole 122 partially expose a lower face of the second insulation layer 130 which is formed on an upper face of the first insulation layer 120. In other words, as shown in FIG. 1, the second insulation layer 130 is formed on the upper face of the first insulation layer 120 to cover the exposure hole 122.

In an example embodiment, each of the cavity 112 and the exposure hole 122 may have a cylindrical shape as shown in FIG. 2 and the shape of each of the cavity 112 and the exposure hole 122 is not restricted to be able to vary.

The heating electrode 142 may be formed on an upper face of the second insulation layer 130. The heating electrode 142 is positioned on the second insulation layer 130 to correspond to the cavity 112 in a vertical direction. The heating electrode 142 can generate heat for the detection layer 180 to detect gas. The heat can be efficiently dissipated through the cavity 112, thus the semiconductor gas sensor can be prevented from damage which may occur by heat, and can maintain a temperature suitable for the detection layer 180 to detect gas. Even though not shown in detail, the heating electrode 142 is electrically connected to a heating pad 144. The heating pad 144 may be formed on the second insulation layer 130 and outside of a portion of the second insulation layer 130, corresponding to the cavity 112. The heating pad 144 may receive a power from an external source to transmit the power to the heating electrode 142.

In an example embodiment, the heating electrode 142 and the heating pad 144 may be formed using platinum (Pt) or tungsten (W).

A third insulation layer 150 may be formed on an upper face of the second insulation layer 130 on which the heating electrode 142 and the heating pad 144 are formed. The third insulation layer 150 may cover the heating electrode 142 and the heating pad 144. The third insulation layer 150 may have a thickness higher than those of the first and the second insulation layers 120 and 130 to be configured to planarize an upper face of the semiconductor gas sensor 100.

As described above, the semiconductor gas sensor includes the second and the third insulation layers 130 and 150 even at a portion corresponding to the cavity 112 to form a membrane structure at the portion corresponding to the cavity 112.

Especially, the layers such as the first to the third insulation layers 120, 130 and 150 may be weak against a thermal stress, and a portion of the layers, corresponding to the cavity 112 in a vertical direction, may not be securely supported by the substrate 110. Thus, a membrane portion of the second and the third insulation layers 130 and 150, corresponding to the cavity 112, may sag down toward the cavity 112 such that the undesirable sag phenomenon described above may occur.

In an example embodiment, the semiconductor gas sensor 100 may relieve the sag of the membrane owing to the exposure hole 122. That is, as shown in FIG. 2, the exposure hole 122 may be formed to have a size larger than that of the cavity 112 such that a portion of the second insulation layer 130 to cover the exposure hole 122 may gradually sag along a fluent curve when the portion of the second insulation layer 130 is bent toward the cavity 112. Thus, the semiconductor gas sensor 100 can relieve a stress of the membrane, compared with the conventional art, to maintain a uniform resistance of the heating electrode 142.

In an example embodiment, the semiconductor gas sensor may further include at least one protrusion portion 132 to relieve the stress of the membrane additionally. The protrusion portion 132 may protrude from the lower face of the second insulation layer 130 to be integrally formed with the second insulation layer 130. The protrusion portion 132 may be positioned to correspond to the peripheral portion of the cavity 112. The protrusion portion 132 may be formed outside from the cavity 112 and inside of the exposure hole 122, and may face the substrate 110 as shown in FIG. 2

In an example embodiment, when a plurality of the protrusion portions 132 is formed as shown in FIGS. 1 and 2, the protrusion portions 132 are apart from the first insulation layer 120, and the protrusion portions 132 are spaced apart from one another and are arranged along a circumferential line of the cavity 112. Further, the protrusion portions 132 may have various shapes such as a cylindrical shape, a pillar shape, a hemispherical shape, etc.

The protrusion portions 132 may support the second insulation layer 130 in order for the second insulation layer 130 positioned over the cavity 112 not to be bent toward the cavity 112. In other words, when the membrane is not bent to keep straight in a horizontal direction, the protrusion portions 132 are spaced apart from the upper face of the substrate 110. On the other hand, when the membrane sags, the protrusion portions 132 make contact with the upper face of the substrate 110 to support the second insulation layer 130 and prevent the second insulation layer 130 from being additionally bent. Thus, the stress of the membrane can be relieved such that the semiconductor gas sensor 100 in accordance with example embodiments can alleviate the sag of the membrane.

In an example embodiment of the present invention, the semiconductor gas sensor 100 may include the sensing electrode 162 formed on an upper face of the third insulation layer 150. The sensing electrode 162 may be positioned to correspond to the cavity 112 and may be formed over the heating electrode 142 in the vertical direction. Even though not shown in FIG. 1 in detail, the sensing electrode 162 may be electrically connected to a sensing pad 164. The sensing pad 164 may be positioned on the upper face of the third insulation layer 150 and away from a portion of the third insulation layer 150 corresponding to the exposure hole 122.

In an example embodiment, the sensing electrode 162 and the sensing pad 164 may include platinum (Pt).

The detection layer 180 is formed on the upper face of the third insulation layer 150 including the sensing electrode 162 and the sensing pad 164. The fourth insulation layer 170 may be formed by removing a portion corresponding to the cavity 112 and may cover the sensing pad 164.

In an example embodiment, the first to the fourth insulation layers 120, 130, 150 and 170 may be formed by depositing silicon oxide material and silicon nitride material in turn. For example, the first and the third insulation layers 120 and 150 include silicon oxide and the second and the fourth insulation layers 130 and 170 include silicon nitride.

The detection layer 180 is formed over the cavity 112 to cover the sensing electrode 162. The detection layer 180 may be formed using oxide semiconductor material such as tin oxide ($SnO_2$) to detect a predetermined kind of gas. In particular, when the detection layer 180 is exposed to the predetermined kind of gas, the gas is adsorbed to a surface of the detection layer 180 to have the resistance of the detection layer 180 varied due to an adsorption reaction. As an output value of the sensing electrode 162 varies according to a change of the resistance value of the detection layer 180, the semiconductor gas sensor 100 can detect whether the gas is in contact with sensing electrode 162, in accordance with the output value of the sensing electrode 162.

Especially, the detection layer 180 may be required to be maintained over a standard temperature in order to make the detection layer 180 sufficiently react with the predetermined gas. The heating electrode(s) 142 may transmit heat into the detection layer 180. Here, the standard temperature may be about 300° C.

The third and the fourth insulation layers 150 and 170 may have a first contact hole 152 to partially expose the heat pad 144. The first contact hole may be formed by partially removing the third and the fourth insulation layers 150 and 170. The fourth insulation layer 170 may have a second contact hole 172 to partially expose the sensing pad 164. The second contact hole 172 may be formed by partially removing the fourth insulation layer 170.

A heating pad electrode 192 and a sensing pad electrode 194 may be formed on the fourth insulation layer 170. The heating pad electrode 192 may be positioned to correspond to the heating pad 144 in the vertical direction to cover the heating pad 144 exposed by the first contact hole 152. The sensing pad electrode 194 may be positioned to correspond to the sensing pad 164 in the vertical direction to cover the sensing pad 164. The heating pad electrode 192 and the sensing pad electrode 194 may include transparent electrodes.

According to example embodiments, the semiconductor gas sensor 100 includes the exposure hole 122 and the protrusion portions 132 to relieve the stress of the membrane and the sag of the membrane. Thus, the heating electrode 142 can keep the resistance uniform to transmit uniform heat into the detection layer 180 and to maintain the temperature of the detection layer 180 constant. Further, since an area to which the heating electrode 142 transmits heat can be kept without a change, heat can be securely given to a sensing area (SA) of the detection layer 180 to retain a uniform temperature distribution. As a result, the semiconductor gas sensor 100 can obtain a secure durability against heat, can be prevented from thermal damage and thus, can detect heat stably.

FIGS. 3 to 7 are cross-sectional views illustrating a method of manufacturing a semiconductor gas sensor in accordance with an example embodiment of the present invention.

Figure 3:
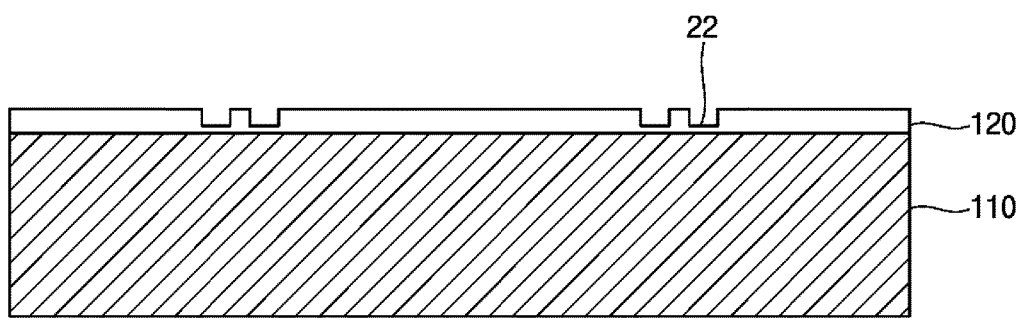
FIGS. 3 to 7 are cross-sectional views illustrating a method of manufacturing a semiconductor gas sensor in accordance with an example embodiment of the present invention.
Figure 4:
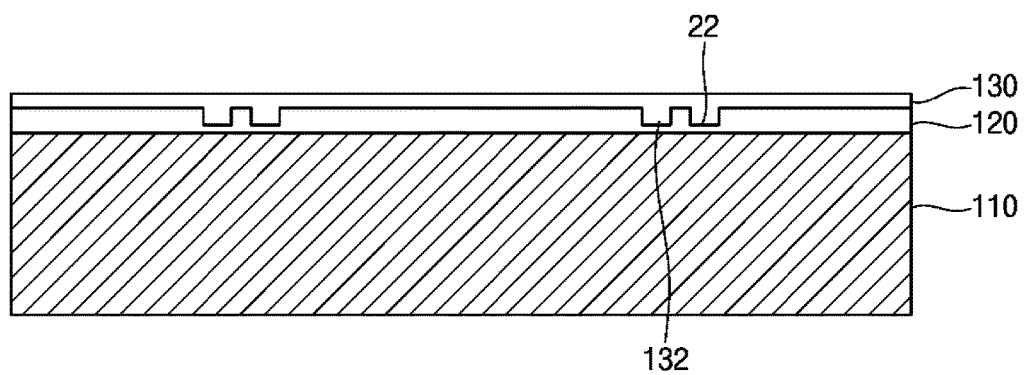

Referring to FIGS. 3 and 4, a first insulation layer 120 is formed on an upper face of a substrate 110. Here, the substrate 110 may include silicon on insulator (SOI) substrate including the first insulation layer 120.

A second insulation layer 130 is formed on an upper face of the first insulation layer 120.

Figure 5:
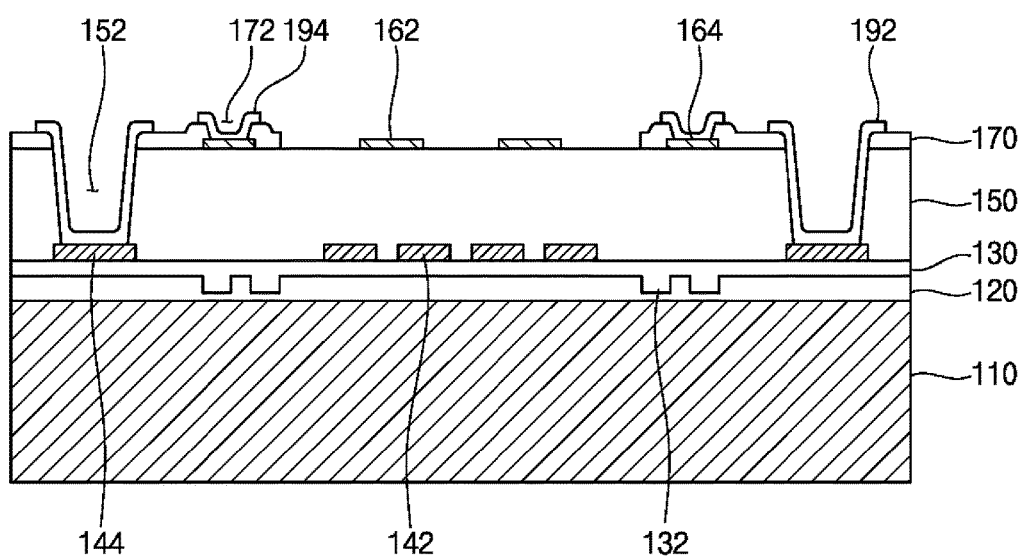

Referring to FIG. 5, after a heating electrode 142 and a heating pad 144 are formed on the second insulation layer 130, a third insulation layer 150 is formed on the second insulation layer 130. After a sensing electrode 162 and a sensing pad 164 are formed on an upper face of the third insulation layer 150, the fourth insulation layer 170 is formed on the third insulation layer 150. The third insulation layer 150 and the fourth insulation layer 170 are patterned to form a first contact hole 152 and a second contact hole 172, respectively. The fourth insulation layer 170 is partially removed at a position corresponding to a cavity (112, see FIG. 1) which is to be formed in a subsequent step of patterning the substrate 110, and a heating pad electrode 192 and a sensing pad electrode 194 may be additionally formed on an upper face of the fourth insulation layer 170.

Figure 6:
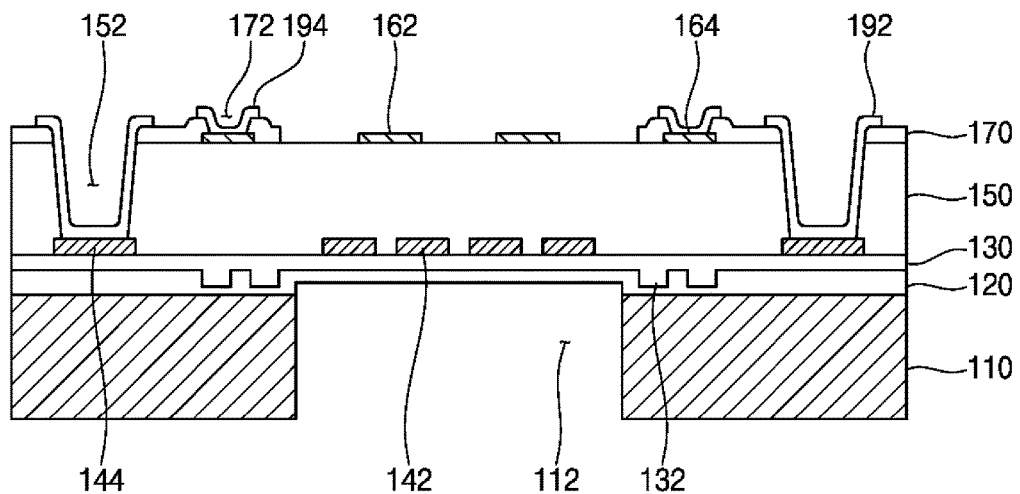

Referring to FIG. 6, after the heating pad electrode 192 and the sensing pad electrode 194 are formed, the substrate 110 is partially etched to form the cavity 112. A portion of the first insulation layer 120, corresponding to the cavity 112 may be removed with patterning the substrate 110.

In an example embodiment of the present invention, the method of manufacturing a semiconductor gas sensor includes a process to polish an lower surface of the substrate 110 to control a thickness of the substrate 110 to make a thickness of the semiconductor gas sensor 110 suitable, prior to the process of forming the cavity 112.

Figure 7:
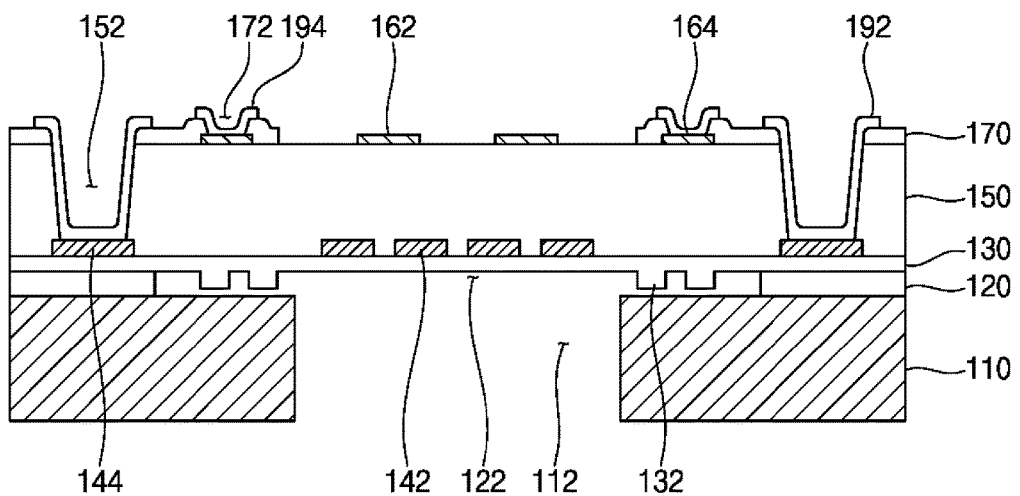

Referring to FIG. 7, after forming the cavity 112 in the substrate 110, the first insulation layer 120 is patterned through an etch process using the cavity 112 to form an exposure hole 122. In detail, the first insulation layer 120 is patterned through the etch process using the substrate 110 as an etch mask, a portion of the first insulation layer 120, exposed by the cavity 112 and adjacent to the cavity 112 is removed to form the exposure hole 122. The size of the exposure hole 122 may be controlled according to a processing time of the etch process.

The second insulation layer 130 formed on the first insulation layer 120 may be formed using a material different from that of the first insulation layer 120 to have an etch selectivity against the first insulation layer 120. Thus, the second insulation layer 130 may not be etched to an etchant for etching the first insulation layer 120. As a result, when forming the exposure hole 122 by partially etching the first insulation layer 120 using an etchant, the second insulation layer 130 may be little acted with the etchant such that the first insulation layer 120 can be selectively etched and patterned.

In an example embodiment, the exposure hole 122 may be formed through a wet etch process.

Referring to FIGS. 3, 4, and 6, a method of manufacturing a semiconductor gas sensor according to an example embodiment include a process of patterning the first insulation layer 120 for forming at least one protrusion portion 132, prior to the process of forming the second insulation layer 130.

In detail, as shown in FIG. 3, the first insulation layer 120 is patterned to form at least one mold hole 22 for forming the protrusion portion 132 on an upper portion of the first insulation layer 120. As shown in FIG. 6, a plurality of mold holes 22 is formed to be spaced apart from one another along a circumferential line of the cavity 112 to surround a portion of corresponding to the cavity 112. Here, each of the mold holes 22 may have a recess shape such that the protrusion portions 132 are spaced apart from the upper face of the substrate 110.

After patterning the first insulation layer 120, a second insulation layer 130 is formed on an upper face of the upper face of the first insulation layer 120. As shown in FIG. 4, the second insulation layer 130 is formed on the first insulation layer 120 with filling up the mold holes 22 to transform portions of filling the mold holes 22 into protrusion portions 132.

Referring to FIGS. 6 and 7, the mold holes 22 of the first insulation layer 120 may be removed from the first insulation layer 120 while forming the exposure hole 122. As a result, a portion of the first insulation layer 120 adjacent to the protrusion portions 132 is removed such that the protrusion portions 132 are positioned in the exposure hole 122. A portion of the first insulation layer 120, which is positioned between the protrusion portions 132 and the substrate 110, is also removed to form a space between the protrusion portions 132 and the substrate 110.

Further, after forming the exposure hole 122, a detection layer 180 (see FIG. 1) is formed on the third insulation layer 150 to complete processes of manufacturing the semiconductor gas sensor 100.

Figure 8:
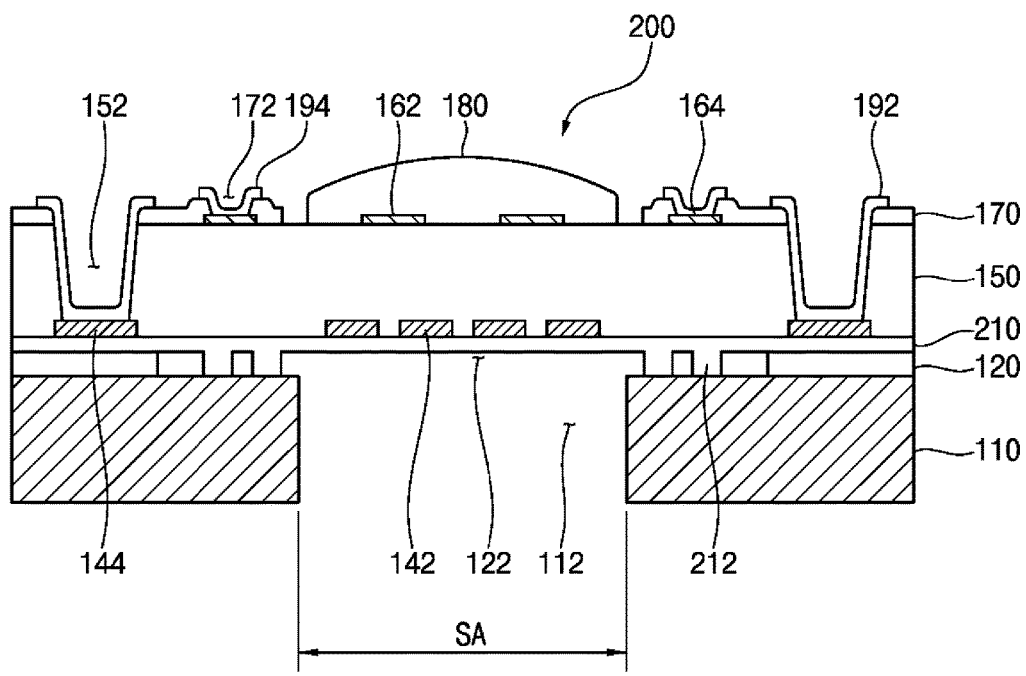
FIG. 8 is a cross-sectional view a semiconductor gas sensor in accordance with an example embodiment of the present invention.

FIG. 8 is a cross-sectional view a semiconductor gas sensor in accordance with an example embodiment of the present invention.

Referring to FIG. 8, a semiconductor gas sensor in accordance with an example embodiment is the same as in the semiconductor gas sensor described with the reference of FIG.1 except for a second insulation layer 210. Thus, the same reference numerals will be used to refer to the same elements having a similar structure and/or function as in FIG. 1. So any further description about the same elements will be omitted to avoid any redundancy.

In particular, a second insulation layer 210 of the semiconductor gas sensor 200 is formed on an upper face of a first insulation layer 120. The second insulation layer 210 includes a plurality of protrusion portion 212 at a lower face thereof. The protrusion portions 212 are positioned to correspond to a peripheral portion of the cavity 112 and may be integrally formed with the second insulation layer 210. The protrusion portions 212 is disposed in the exposure hole 122.

The protrusion portions 212 makes contact with an upper face of the substrate 110 to support the second insulation layer 210 to relieve sag of a membrane which means a stacked portion of the first insulation layer 210 and the third insulation layer 150 corresponding to the cavity 112.

In an example embodiment, the protrusion portions 212 may have various shapes such as a cylindrical shape, a pillar shape, hemispherical shape, etc. The protrusion portions 212 may be spaced apart from one another along a circumferential line of the cavity 112.

Figure 9:
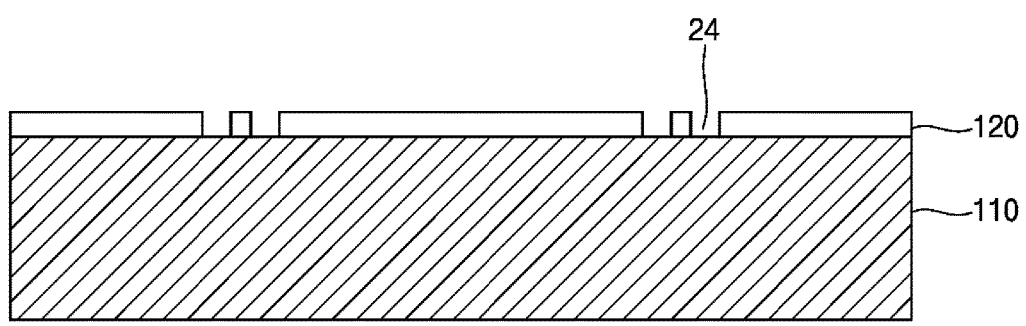
FIGS. 9 and 10 are cross-sectional views illustrating a method of manufacturing a semiconductor gas sensor in accordance with an example embodiment of the present invention.
Figure 10:
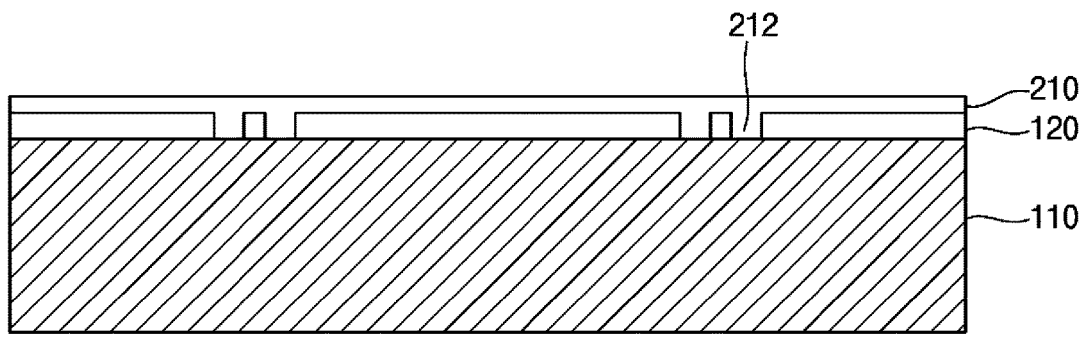

FIGS. 9 and 10 are cross-sectional views illustrating a method of manufacturing a semiconductor gas sensor in accordance with an example embodiment of the present invention.

Referring to FIGS. 9 and 10, a first insulation layer 120 formed on a substrate 110 is patterned to form a plurality of mold holes 24 for forming protrusion portions 212. Each of the mold holes may have a type of a penetration hole in order for the protrusion portions 212 to make contact with an upper face of the substrate 112, such that a portion of substrate 110 is exposed through the mold holes 24.

After patterning the first insulation layer 120, a second insulation layer is formed on an upper face of the first insulation layer 120 to form the protrusion portions 212 by filling up the mold holes 24 with the second insulation layer 210.

A method of manufacturing a semiconductor gas sensor in accordance with an example embodiment includes steps which are the same as in the method of manufacturing the semiconductor gas sensor described with the reference of FIGS. 5 to 7 except for a step for patterning the first insulation layer 120. Thus, any further description about the same step after patterning the first insulation layer 120 will be omitted to avoid any redundancy.

Although the semiconductor gas sensors have been described with reference to the specific embodiments, they are not limited thereto. Therefore, it will be readily understood by those skilled in the art that various modifications and changes can be made thereto without departing from the spirit and scope of the appended claims.

What is claimed is:

1. A semiconductor gas sensor comprising:
   a substrate defining a cavity that extends to a peripheral portion;
   a first insulation layer formed on the substrate and defining an exposure hole adjacent to the cavity and the peripheral portion;
   a second insulation layer formed on the first insulation layer and arranged at the exposure hole opposite from the cavity;
   a heating electrode formed on the second insulation layer on a surface opposite from the exposure hole and the cavity;
   a sensing electrode arranged opposite the heating electrode from the exposure hole and the cavity, wherein the sensing electrode is electrically insulated from the heating electrode;
   a detection layer covering the sensing electrode and having a variable resistance when interacting with a predetermined gas; and
   at least one protrusion portion protruded from a lower face of the second insulation layer, the protrusion portion being formed at a position corresponding to the peripheral portion of the cavity and configured to at least partially prevent the second insulation layer from sagging down to the cavity.

2. The semiconductor gas sensor of claim 1, wherein each of the cavity and the exposure hole has a cylindrical shape.

3. The semiconductor gas sensor of claim 1, further comprising:
   a heating pad formed on the second insulation layer and out of the exposure hole, the heating pad being electrically connected to the heating electrode;
   a sensing pad formed being coplanar with the sensing electrode, the sensing pad being electrically connected with the sensing electrode; and
   a third insulation layer being formed on the second insulation layer having the heating electrode and the heating pad, and including a first face remote from the heating pad and on which the sensing electrode and the sensing pad is formed, such that the third insulation layer insulates the heating electrode from the sensing electrode.

4. The semiconductor gas sensor of claim 1, wherein one of the first and the second insulation layers includes silicon oxide, the other of the first and the second insulation layers includes silicon nitride.

5. The semiconductor gas sensor of claim 1, wherein the protrusion portion is formed in the exposure hole protruding from the lower face towards the substrate.

6. The semiconductor gas sensor of claim 5, wherein the protrusion portion is spaced apart from an upper face of the substrate.

7. The semiconductor gas sensor of claim 5, wherein the protrusion portion makes contact with the substrate.

8. The semiconductor gas sensor of claim 5, wherein a plurality of protrusion portions is formed along a circumferential line of the cavity and spaced apart from one another.

9. The semiconductor gas sensor of claim 5, wherein the protrusion portion is spaced apart from the first insulation layer.

10. The semiconductor gas sensor of claim 5, wherein the protrusion portion has a column shape.

11. The semiconductor gas sensor of claim 5, wherein the protrusion portion is integrally formed with the second insulation layer.

12. A method of manufacturing a semiconductor gas sensor comprising:
   forming a first insulation layer on a face of a substrate;
   forming a second insulation layer on the first insulation layer;
   forming a heating electrode on the second insulation layer opposite the first insulation layer, the heating electrode being capable of generating heat;
   forming a sensing electrode insulated from the heating electrode;
   patterning the substrate to form a cavity under the heating electrode;
   removing a portion of the first insulation layer which is exposed by the cavity and corresponds to a peripheral portion of the cavity to form an exposure hole;
   forming a detecting electrode covering the sensing electrode, the detecting electrode having a variable resistance when interacting with a predetermined kind of gas; and
   forming at least one protrusion portion protruded from a lower face of the second insulation layer, the protrusion portion being formed at a position corresponding to the peripheral portion of the cavity and configured to at least partially prevent the second insulation layer from sagging down to the cavity.

13. The method of claim 12, wherein forming the heating electrode includes forming a heating pad on the second insulation layer and opposite from the exposure hole, the heating pad being electrically connected with the heating electrode, and wherein forming the sensing electrode includes forming a sensing pad electrically connected with the sensing electrode.

14. The method of claim 12, wherein forming the exposure hole includes patterning the first insulation layer through a wet etch process using the substrate having the cavity as an etch mask.

15. The method of claim 12, wherein the first insulation layer is formed using a material different from that of the second insulation layer.

16. The method of claim 12, further comprising:
   prior to forming the second insulation layer, patterning the first insulation layer to form at least one mold hole for forming the protrusion portion at a face of the second insulation layer,
   wherein the mold hole is formed at a position corresponding to the peripheral portion of the cavity and a portion of the first insulation layer, and
   forming the exposure hole includes forming the protrusion portion in the exposure hole by removing a portion of the first insulation layer adjacent to the protrusion portion.

17. The method of claim 16, wherein the mold hole has a recess shape such that the protrusion portion is apart from the substrate.

18. The method of claim 16, wherein the mold hole has a penetration-hole shape to partially expose the substrate, such that the protrusion portion makes contact with the substrate.

19. The method of claim 16, wherein a plurality of mold holes surrounds a portion of the first insulation layer corresponding to the cavity, and each of the protrusion portions are apart from one another.

* * * * *